(12) United States Patent
Reiderman et al.

(10) Patent No.: US 10,222,505 B2
(45) Date of Patent: Mar. 5, 2019

(54) COMBINED NMR-RESISTIVITY MEASUREMENT APPARATUS, SYSTEMS, AND METHODS

(71) Applicant: Halliburton Energy Services, Inc., Houston, TX (US)

(72) Inventors: Arcady Reiderman, Katy, TX (US); Songhua Chen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 141 days.

(21) Appl. No.: 15/118,059

(22) PCT Filed: Dec. 30, 2014

(86) PCT No.: PCT/US2014/072777
§ 371 (c)(1),
(2) Date: Aug. 10, 2016

(87) PCT Pub. No.: WO2016/108851
PCT Pub. Date: Jul. 7, 2016

(65) Prior Publication Data
US 2018/0074221 A1    Mar. 15, 2018

(51) Int. Cl.
*G01R 33/34* (2006.01)
*G01V 3/32* (2006.01)
(Continued)

(52) U.S. Cl.
CPC ............. *G01V 3/32* (2013.01); *G01N 24/081* (2013.01); *G01R 33/34053* (2013.01);
(Continued)

(58) Field of Classification Search
CPC ....... G01V 3/28; G01V 3/32; G01R 33/34069
(Continued)

(56) References Cited

U.S. PATENT DOCUMENTS

| 5,814,988 A | 9/1998 | Itskovich et al. |
| 5,818,232 A * | 10/1998 | Mehr ............... G01R 33/34046 |
| | | 324/314 |

(Continued)

FOREIGN PATENT DOCUMENTS

| GB | 2311864 A | 10/1997 |
| WO | WO 2013165428 A1 * | 11/2013 ............. E21B 49/00 |

(Continued)

OTHER PUBLICATIONS

"International Application Serial No. PCT/US2014/072777, International Search Report dated Sep. 3, 2015", 3 pgs.
(Continued)

*Primary Examiner* — Melissa J Koval
*Assistant Examiner* — Rahul Maini
(74) *Attorney, Agent, or Firm* — Gilliam IP PLLC (57) ABSTRACT

In some embodiments, an apparatus, system, and method may operate to transmit, using a first transceiver antenna, a common signal into a geological formation, and to receive in response to the transmitting, at the first transceiver antenna, a first corresponding nuclear magnetic resonance (NMR) signal from a first volume of the formation. Additional activity may include receiving, in response to the transmitting, at a second transceiver antenna spaced apart from the first transceiver antenna, the common signal transformed by the formation into a received resistivity signal, as well as transmitting, using the second transceiver antenna, a second corresponding NMR signal into a second volume of the formation different from the first volume of the formation. Additional apparatus, systems, and methods are disclosed.

19 Claims, 9 Drawing Sheets

(51) Int. Cl.
*G01V 3/28* (2006.01)
*G01N 24/08* (2006.01)
*G01R 33/36* (2006.01)
*G01R 33/38* (2006.01)
*G01R 33/44* (2006.01)

(52) U.S. Cl.
CPC ......... *G01R 33/34069* (2013.01); *G01V 3/28* (2013.01); *G01R 33/3678* (2013.01); *G01R 33/3808* (2013.01); *G01R 33/443* (2013.01)

(58) Field of Classification Search
USPC ........................................................ 324/303
See application file for complete search history.

(56) References Cited

U.S. PATENT DOCUMENTS

| | | | |
|---|---|---|---|
| 5,828,214 A | 10/1998 | Taicher et al. | |
| 5,831,433 A | 11/1998 | Sezginer et al. | |
| 5,879,300 A * | 3/1999 | Gilderdale | G01R 33/34069 324/318 |
| 6,459,262 B1 * | 10/2002 | Wisler | G01V 3/32 324/303 |
| 6,781,371 B2 * | 8/2004 | Taherian | G01V 3/32 324/303 |
| 7,463,027 B2 * | 12/2008 | Prammer | G01V 3/32 324/303 |
| 7,612,565 B2 * | 11/2009 | Seydoux | G01V 3/28 324/334 |
| 8,612,156 B2 | 12/2013 | Gulati | |
| 8,633,689 B2 * | 1/2014 | Li | G01N 24/081 324/306 |
| 2005/0030021 A1 | 2/2005 | Prammer et al. | |
| 2009/0091327 A1 | 4/2009 | Blanz | |
| 2009/0105955 A1 | 4/2009 | Castillo et al. | |
| 2011/0180327 A1 | 7/2011 | Bittar et al. | |
| 2013/0093422 A1 * | 4/2013 | Morys | G01V 3/32 324/303 |

FOREIGN PATENT DOCUMENTS

| | | |
|---|---|---|
| WO | WO-2014137863 A2 | 9/2014 |
| WO | 2015031027 A1 | 3/2015 |
| WO | WO-2016108851 A1 | 7/2016 |

OTHER PUBLICATIONS

"International Application Serial No. PCT/US2014/072777, Written Opinion dated Sep. 3, 2015", 5 pgs.
CA Application Serial No. 2,965,794, First Office Action, dated Mar. 12, 2018,, 4 pages.
EP Application Serial No. 14909654.7, Extended European Search Report, dated Jul. 17, 2018, 9 pages.

* cited by examiner

COMBINED NMR-RESISTIVITY MEASUREMENT APPARATUS, SYSTEMS, AND METHODS

BACKGROUND

Understanding the structure and properties of geological formations may reduce the cost of drilling wells for oil and gas exploration. Measurements are typically performed in a borehole (i.e., down hole measurements) in order to attain this understanding. For example, the measurements may identify the composition and distribution of material that surrounds the measurement device down hole. To obtain such measurements, a variety of sensors and mounting configurations may be used. These apparatus include antennae that are used to provide nuclear magnetic resonance (NMR) measurements, and antennae to provide resistivity measurements.

DETAILED DESCRIPTION

In order to characterize subsurface formations while drilling a well in a geological formation, it is common to rely on different measurements and their integrated interpretation, such as NMR measurements and resistivity measurements. Both can be effectively used, for example, to geo-steer the drill bit along a desired well path. Other measurements can also be made, and the values of such measurements are often stored in a log as drilling progresses.

The size, complexity, and cost of commercial well logging wile drilling (LWD) tools are considered important by the consumer of LWD services. This consideration moderates the ability to gain more and better information that might be provided as new instruments are added to the subsurface tool string. This is because each additional LWD tool increases the overall length, complexity, and cost of the string. Moreover, it is often useful to locate LWD tools as close as possible to the drill bit, placing instruments in competition with each other for space. Thus, the desire to reduced size, complexity and cost may conflict with the desire to provide detailed information about the formation surrounding the well.

To address this problem, existing approaches provide resistivity measurements that are made using an NMR sensor in conjunction with multiple resistivity sensors. However, the use of additional resistivity sensors does not provide much of a practical advantage over the more conventional method that employs two separate instruments in the logging string. Thus, there is a need for improvements in combined NMR/resistivity measurements, so that a reduced number of sensor on a single tool can be used to cover multiple NMR sensitivity volumes.

For the purposes of this document, an "NMR signal" comprises a voltage induced in an antenna by nuclear magnetization of atoms in a geological formation proximate to the antenna. A "resistivity signal" comprises a voltage induced in an antenna resulting from eddy currents in the formation. A "transceiver antenna" is an antenna that is capable of emitting a common signal in the form of radio-frequency pulses or continuous waves, and capable of receiving NMR and resistivity signals resulting from a common signal emitted by the same or another transceiver antenna. A "common signal" is signal which is capable of entering a formation as an RF pulse sequence that can excite both NMR, and currents from which resistivity can be determined. Thus, a common signal comprises an RF pulse sequence; or an RF pulse sequence on one carrier frequency, and a CW signal on another carrier frequency. The CW signal may also be generated at the same frequency during time intervals between the RF pulse sequences that are used for NMR excitation.

Figure 1:
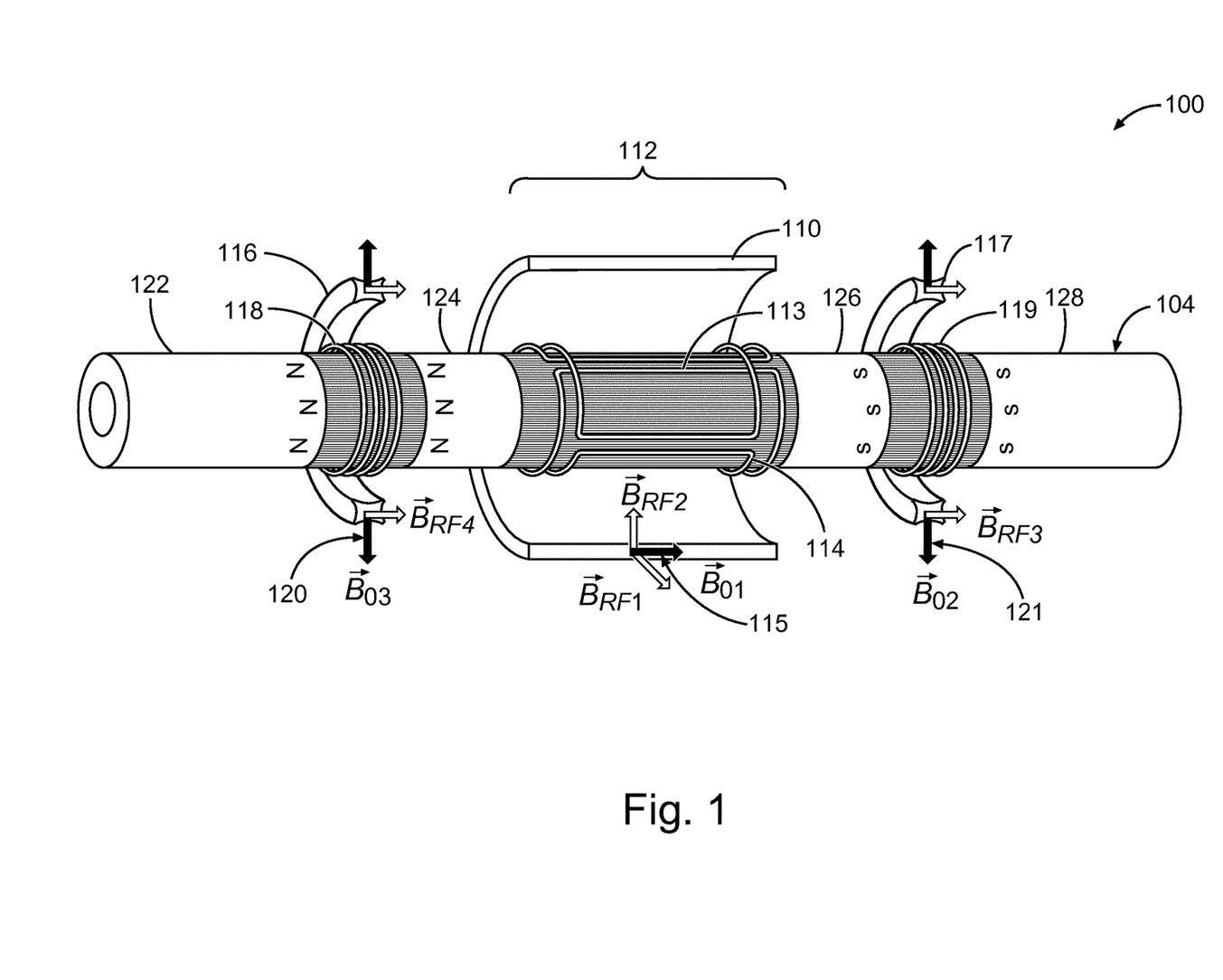
FIG. 1 is a perspective view of transceiver antennae attached to a housing, according to various embodiments of the invention.

FIG. 1 is a perspective view of transceiver antennae 113, 114, 118, 119 attached to a common substrate 104, according to various embodiments of the invention. In most embodiments, multi-volume NMR measurements, along with resistivity measurements, can all be made with the transceiver antennae 113, 114, 118, 119. No additional antennae are used for resistivity measurements. Thus, the apparatus 100 may be characterized as a multi-volume NMR sensor.

Different regions of the magnet assembly are used to acquire NMR signals. NMR experiments in these regions can be run simultaneously or sequentially. One sensitive volume 110 is created at the central magnetic field area 112 with a primarily axial component of the static magnetic field. The radio frequency (RF) magnetic fields BRF1 and BRF2 are produced by two transversal dipole antennae 113 and 114. The directions of the RF magnetic field and the static magnetic field $B_{01}$ in this area are shown at 115.

Two more sensitive volumes 116 and 117 are created near the poles of the magnets 122, 124, 126, 128 where the static magnetic fields $B_{02}$ and $B_{03}$ have a predominantly radial component. The transceiver antennae 118, 119 are shown generating RF magnetic fields in the sensitive volumes 116 and 117 as longitudinal-dipole antennae. The directions of the RF magnetic fields and the static magnetic field in the volumes 116 and 117 are shown at 120 and 121. In some embodiments, the RF magnetic fields generated in the volumes of investigation 110, 116, 117 have different excitation frequencies and different depths of investigation. The operating frequency determined by the static magnetic field strength may be in the range about 0.2 MHz to about 1 MHz.

Figure 2:
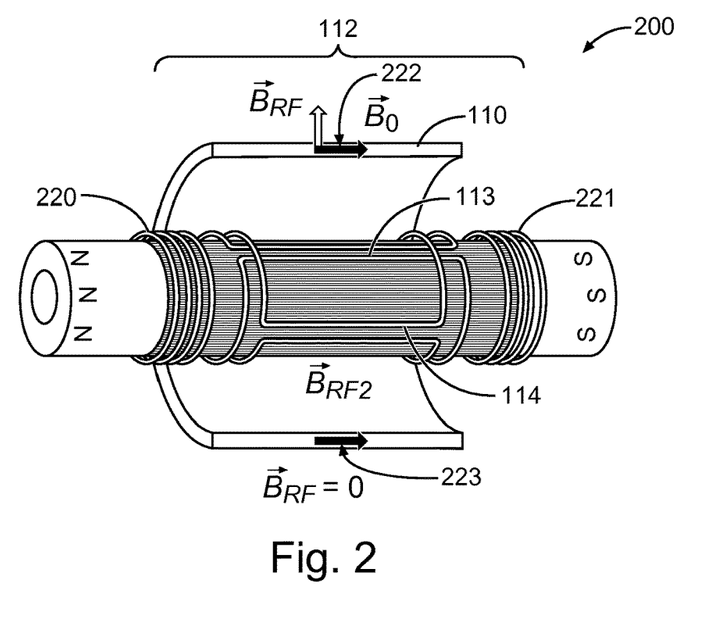
FIG. 2 is a detailed view of an alternative configuration for the central portion of the apparatus shown in FIG. 1.

FIG. 2 is a detailed view of an alternative configuration 200 for the central portion of the apparatus 100 shown in FIG. 1. In this case, two transceiver antennae 220, 221, in the form of coils, have been added to the central portion of the apparatus 100. These antennae 220, 221, when connected in reverse polarity, form a monopole antenna that in combination with the transversal antennae 113, 114 enable unidirectional, azimuthally-selective measurements. Thus, in some embodiments, NMR excitation is substantially axially symmetrical (using either the transversal-dipole antennae 113, 114 or the monopole antenna formed by connecting the antennae 220, 221 in reverse polarity), while the combination of an axially symmetrical sensitivity, transversal-dipole antenna 113 or/and 114, and an axially symmetrical sensitivity monopole antenna, [provided by the combination of antennae 220 and 221 connected in reverse polarity], give a total response that enables azimuthally-resolved measurements.

The monopole-type NMR antenna generates a substantially radial RF magnetic field in the volume of investigation. Due to reciprocity, the same coil arrangement will have a radial sensitivity direction. The RF magnetic field $B_{RF}$ in FIG. 2 presented at field locations 222 and 223 ($B_{RF}=0$ at 223) show the total sensitivity when the monopole antenna response is combined with the response from one of the transversal-dipole antennae 113, 114.

Figure 3:
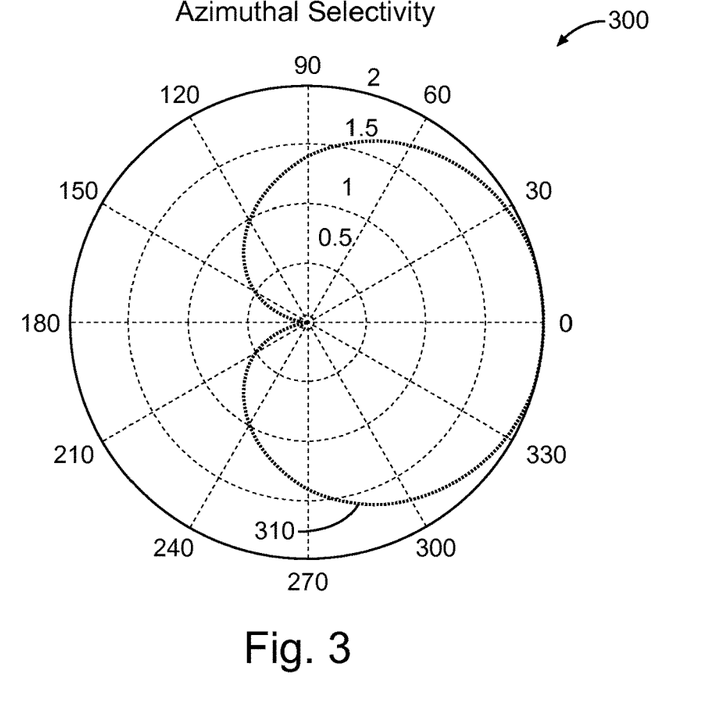
FIG. 3 is a polar plot of azimuthal sensitivity for the portion of the apparatus shown in FIG. 2.

FIG. 3 is a polar plot 300 of azimuthal sensitivity for the portion of the apparatus shown in FIG. 2. The polar plot 300 of antenna sensitivity 310 demonstrates unidirectional azimuthal selectivity. By referring to FIGS. 2 and 3, those of ordinary skill in the art will realize that a proper combination of the responses from each of the orthogonal transversal-dipole antennae 113, 114, and the response of the monopole antenna (combination of antennae 220, 221) can provide sensitivity in any one of four directions, covering all quadrants of the transversal plane. Rotating the apparatus 100 (see FIG. 1) when attached to a drill string or a wireline sonde may be used to cause amplitude modulation of the azimuthally selective response, and therefore, an amplitude modulation of the NMR relaxation signal (e.g. a Car-Purcel-Meiboom-Gill (CPMG) echo train). Measurements of amplitude modulation parameters (e.g., frequency, amplitude) during rotation can be used to indicate azimuthal variations of NMR properties in a formation, such as variations in porosity.

Thus, the monopole antenna resulting from the combination of transceiver antennae 220, 221 can be used in combination with the transversal-dipole antennae 113, 114 to achieve azimuthal selectivity. One of ordinary skill in the art, after reading this disclosure, will understand that the monopole antenna (resulting from the reverse polarity combination of coils making up the transceiver antennae 220, 221) can be also used as separate transceiver antennae, for example, to amplify the received signal and improve the signal-to-noise ratio (SNR). As will be explained later in more detail, the transceiver antennae 220, 221 can also be used individually to make resistivity measurements.

Figure 4:
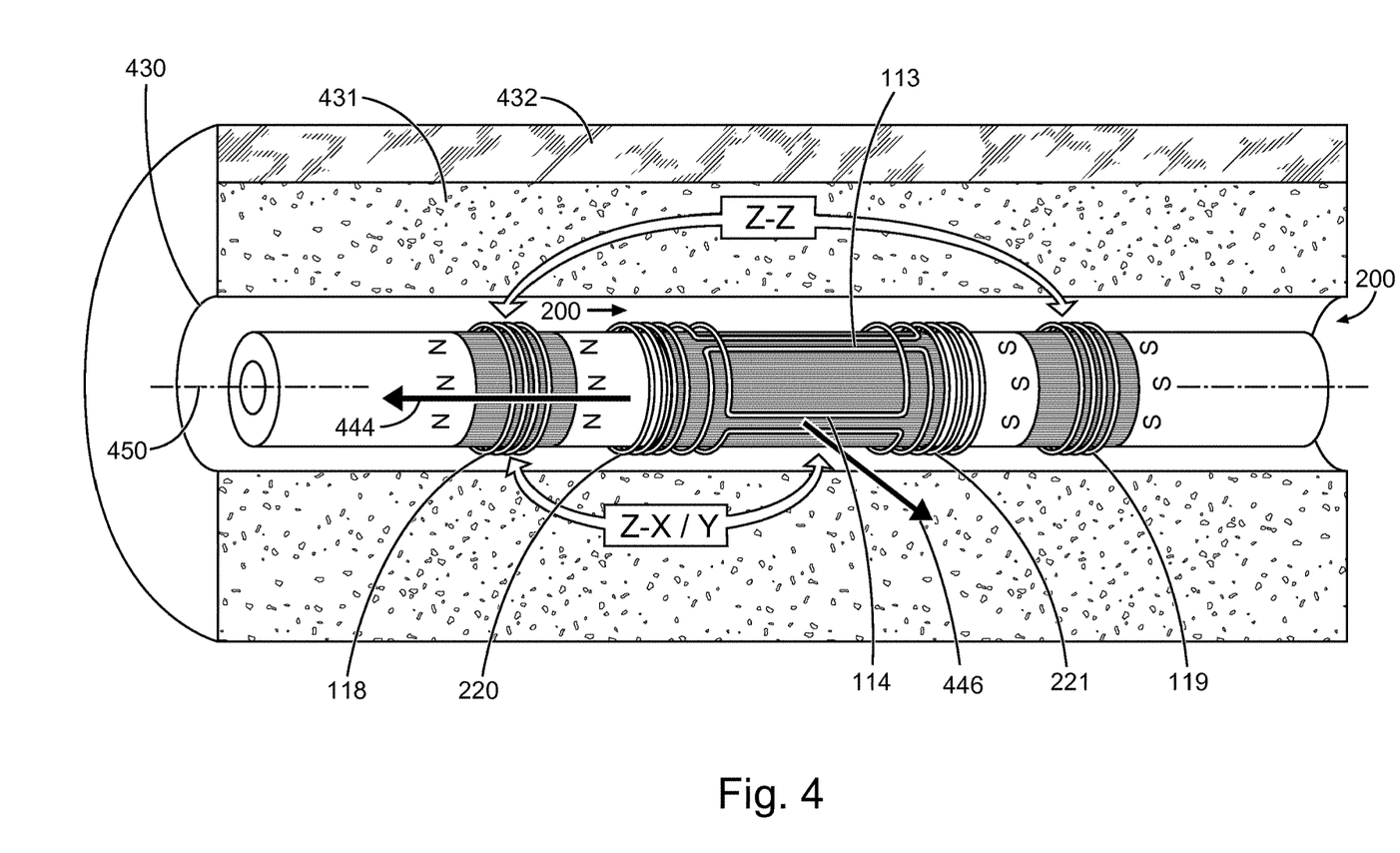
FIG. 4 is a perspective view of the apparatus of FIGS. 1 and 2, applied to carry out multi-volume NMR measurements.

FIG. 4 is a perspective view of the apparatus 100, 200 of FIGS. 1 and 2, applied to carry out multi-volume NMR measurements. The apparatus 100, as noted previously, is capable of making combined NMR and resistivity measurements. Shown here is the apparatus 100 disposed in a well bore 430 (e.g. a vertical or horizontal well that is being created via a drilling process, or an existing vertical or horizontal borehole being examined using a wireline sonde) that traverses a formation 431 in the Earth. Another formation 432 neighbouring the formation 431 presents a different resistivity from the formation 431. In this case, the transceiver antennae 113, 114, 118, 119, 220, 221 can be used as both NMR and resistivity sensors. The two axially spaced longitudinal dipoles presented by transceiver antennae 118, 119, formed as coils, can be used as a Z-Z component transmitter-receiver pair, where Z is the axial component. For example, the transceiver antenna 118 can be used to transmit a combination signal, and while the combination signal is being transmitted, the transceiver antenna 119 can be used to receive the signal as a measurement of resistivity, and then again, to receive an NMR signal after the transceiver antenna 119 has energized the surrounding formation 431 with its own transmission of a combination signal. As a result of transmitting combination signals into the surrounding formation 431, the antennae 113, 114, 118, 119, 220, 221 energize the formation 431 with RF magnetic field pulse sequences, which can ultimately be used to acquire NMR information about the formation 431 and determine the distance to the boundary between the formations 431 and 432. These RF pulse sequences are also suitable for resistivity signal acquisition, as will be explained with respect to FIGS. 5 and 6.

Those of ordinary skill in the art, after reviewing this disclosure, will understand that in addition to the Z-Z resistivity component 444, it can be useful to acquire other components of the resistivity tensor. For example, a Z-Y or Z-X component 446 can provide directional information used to determine the existence of a boundary between high resistivity (e.g. oil reservoir) and low resistivity (e.g., sand and shale) formations above or below the tool position when steering in a horizontal well. The Z-Y and Z-X measurements can be implemented, for example, by using transceiver antennae 113, 114, 118, 119 to receive combination signals, or the result of combination signals that have energized the surrounding formation (to provide NMR measurements). In some embodiments, any of the transceiver antennae 113, 114, 118, 119, 220, 221 can be used to make such measurements.

In conventional applications, an additional antenna coil is used to make resistivity measurements, to measure the Z-Z component (or other diagonal components X-X and Y-Y) of the resistivity tensor. However, a direct field signal is sometimes produced in the receiver coil by the transmitter coil via direct transmitter-receiver induction coupling. If no compensation is made for this effect, the direct field signal often causes errors in determining the amplitude and the phase of the receiver signal that is used to calculate formation resistivity. In an attempt to reduce the effects of direct field signal coupling on the resulting data, the information obtained from the additional receiver coil that is used in conventional applications is processed along with other information.

As a matter of contrast, in various embodiments described herein, transceiver antennae 220, 221 can be used to solve the direct field problem—without the use of extra receivers. For example, the amplitude ratio and phase difference, of and between the received signals in transceivers 221 and 119 when transceiver 118 is used in the transmitting mode can be used to calculate the resistivity of the formation 431, instead of relying solely on the amplitude and phase of the signal received by transceiver antenna 119. In this way, resistivity measurements that are obtained via various embodiments can be made relatively insensitive to the influence of direct field coupling errors.

In conventional resistivity measurement applications, resistivity tools are manufactured so that transmitter and receiver functions are assigned to particular coils. That is, a particular coil operates solely as a transmitter, or a receiver, but not both. In conventional NMR logging tools, the transmitter and receiver functions are assigned to a single coil: the same coil is used to transmit pulsed RF energy, and receive the signal in response to the pulse. A transmit/receive decoupling scheme is typically used to enable this type of operation As a matter of contrast, in various embodiments described herein, each of the transceiver antennae 113, 114, 118, 119 is used not only as a transmitter and receiver for NMR measurements, but also as a transmitter and receiver for resistivity measurements. As transmitters, the transceiver antennae 118, 119, and 113 (or 114) can operate at different frequencies, which enable different depths of investigation in the formation 431 for NMR measurements. The use of these antennae as transceivers provides resistivity data that can be more easily and accurately interpreted.

Given the structure of the apparatus 100, some useful transmit-receive combinations for resistivity measurements might be: (a) using transceiver antenna 118 in a transmission mode, and using transceiver antennae 113, 114, and 119 in a reception mode, all operating at a frequency FREQ1; (b) using transceiver antenna 119 in a transmission mode, and using transceiver antennae 113, 114, and 118 in a reception mode, all operating at a different frequency FREQ2; and (c) using either one of transceiver antennae 113 or 114 in a transmission mode, and using transceiver antennae 118, 119 in a reception mode, all operating at yet another frequency FREQ3. Transceiver antennae 220, 221 can be used in a reception mode to reduce or eliminate effects due to the influence of direct field signal coupling in the resistivity data.

Figure 5:
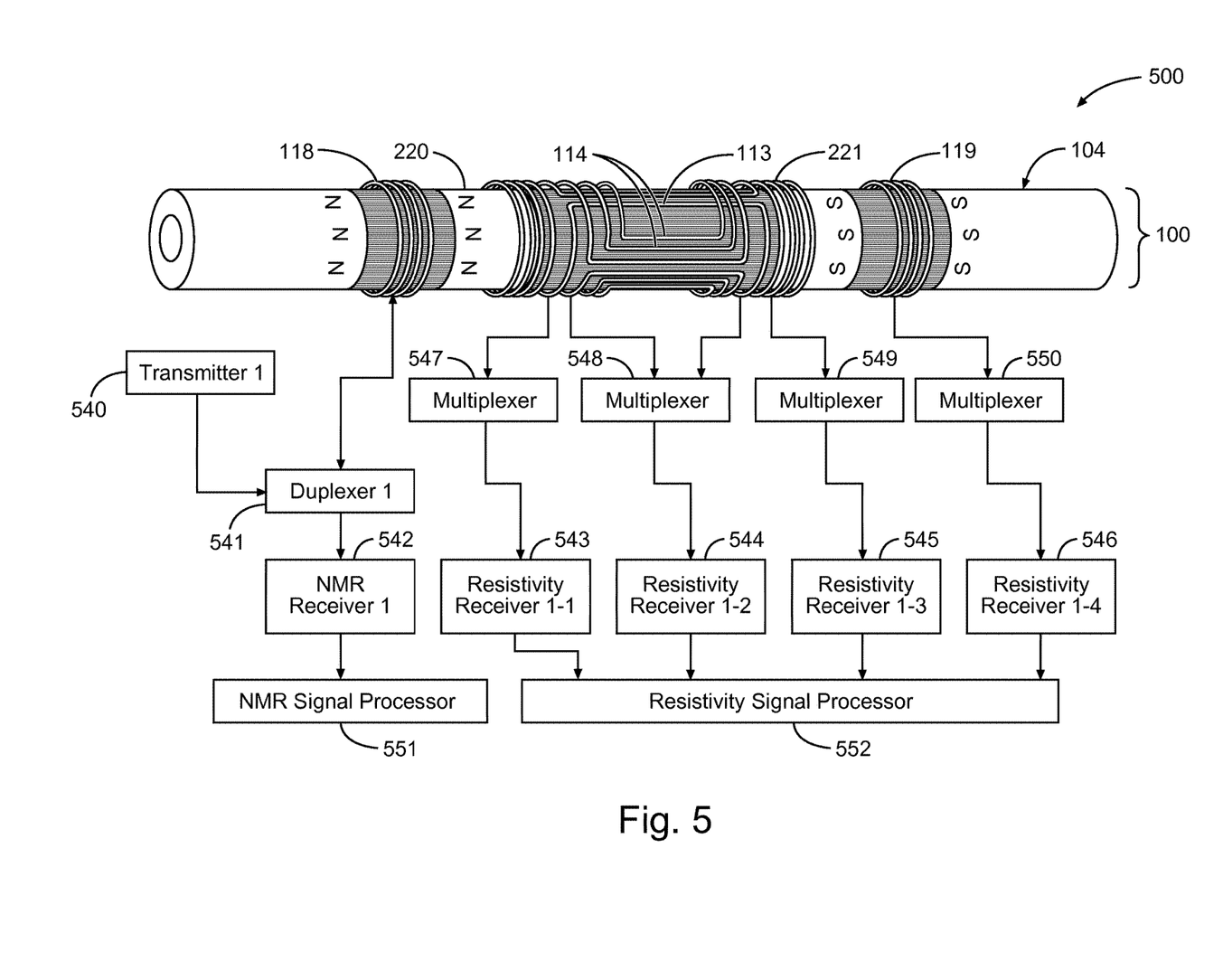
FIG. 5 is a block diagram of the apparatus of FIG. 3, combined with signal switching, transmission, and reception hardware, to form a system, according to various embodiments of the invention.

FIG. 5 is a block diagram of the apparatus 100 of FIG. 3, combined with signal switching, transmission, and reception hardware, to form a system 500, according to various embodiments of the invention. In this figure, an example arrangement of transceiver antennae and switching circuitry is shown to demonstrate operating over a variety of modes. It is noted that many other arrangements are possible.

In this example, the transceiver antenna 118 is used in a transmission mode to deliver combination signals that include RF pulses, and later, in a receiving mode, while the remaining transceiver antennae 113, 114, 119, 220, 221 are used in a receiving mode. For the purposes of this example, this operation occurs at a single frequency FREQ1.

Alternative arrangements can be made with any of the antennae 113, 114, 118, 119, 220, 221, to show operation with each one in a transmission mode, and every transceiver antenna 113, 114, 118, 119, 220, 221, operating in a reception mode, at the appropriate time, to obtain both resistivity and NMR signal information. This operation can occur at the same frequency, or at different frequencies. These numerous possible arrangements, which will easily be understood by those of ordinary skill in the art after reading this disclosure and viewing the drawings, are not shown here in the interest of brevity and clarity.

To continue with the particular example shown in FIG. 5, the transceiver antenna 118 can be used in a reception mode to make NMR measurements, and the transceiver antennae 113, 114, 119, and 221 can be used in a reception mode to make resistivity measurements—all at the same frequency FREQ1. Transmitter drive electronics 540 are electrically coupled to the transceiver antenna 118, which is in turn coupled to an NMR receiver 542, via a duplexer 541. Receivers 543, 544, 545, and 546 are coupled to transceiver antennae 220, 114, 113, and 119 respectively, via multiplexers 547, 548, 549, and 550. An NMR signal processor 551 is used to process the NMR signals received by the transceiver antenna 118, and a resistivity signal processor 552 is used to process the resistivity signals received by the transceiver antennae 220, 114, 113, 221, and 119.

Each of the transceiver antennae 113, 114, 118, 119, 220, or 221 can be connected to NMR transmitter electronics (e.g., transmitter drive electronics 540), NMR receiver electronics (e.g., NMR receiver 542), and/or resistivity receiver electronics (e.g., receivers 543, 544, 545, 546) via use of the multiplexers 547, 548, 549, and 550, to provide a multitude of coupling configurations beyond what is explicitly shown in FIG. 5, as is well known to those of ordinary skill in the art. Additional circuitry, such as damping circuits, matching circuits, sensor tuning circuits, phase sensitive detection circuits, a timing controller, and analog-to-digital converters, well-known to those of ordinary skill in the art, can also be employed to enable such operation. These circuits have not been shown in the figure to promote clarity, and so as not to obscure the explanation of operating various embodiments.

Figure 6:
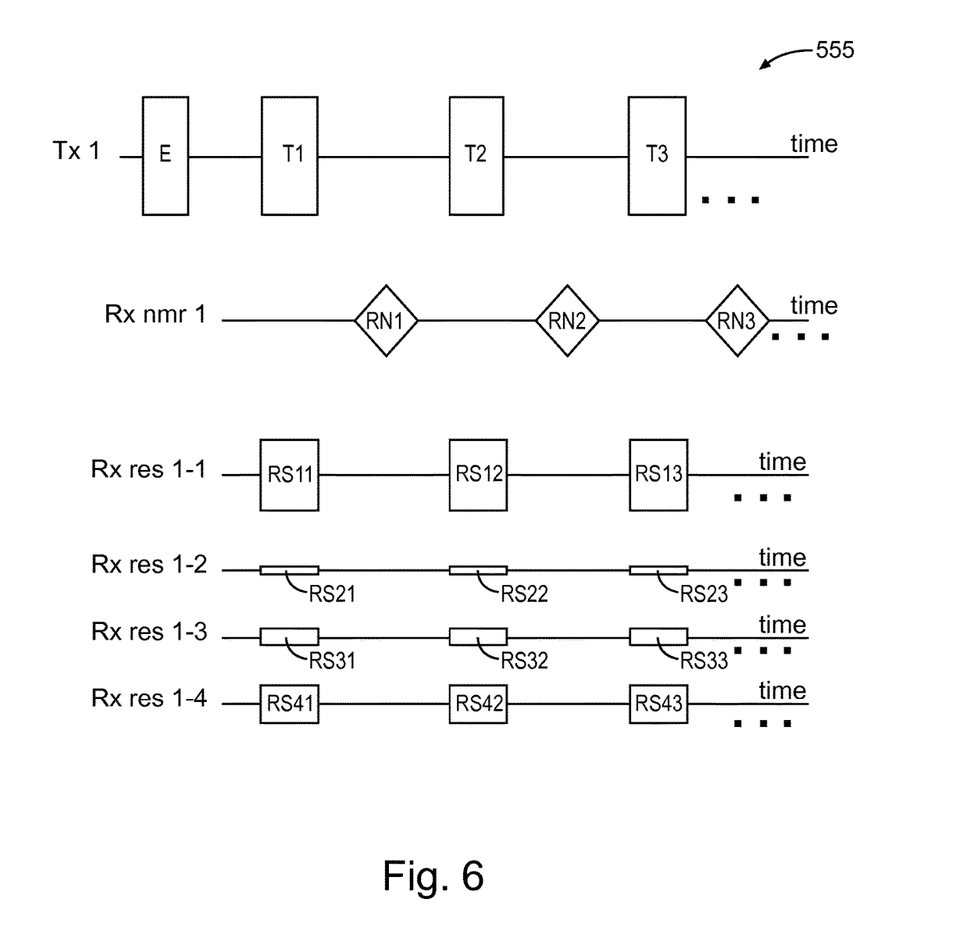
FIG. 6 is a simplified timing diagram for operation of the apparatus and system shown in FIG. 5.

Referring now to FIG. 6, a sequence of RF pulses T1, T2, T3 are generated and used to conduct NMR measurements. An NMR pulse sequence typically consists of one excitation pulse E and a large number of refocusing pulses T1, T2, T3, . . . . By receiving after each of the RF pulses, NMR data is acquired in the form of spin echoes RN1, RN2, RN3, . . . that occur between the refocusing RF pulses T1, T2, T3, . . . . The signal information from the spin echoes RN1, RN2, RN3, . . . is transferred to the NMR signal processor 551 (reference FIG. 5) via the duplexer 541 and receiver 542.

Resistivity signal information can be acquired during the transmission of the NMR refocusing pulses T1, T2, T3, . . . . That is, resistivity signals RS11, RS12, RS13, . . . are acquired during the transmission of NMR refocusing pulses T1, T2, T3, . . . , and not afterward (as occurs for the acquisition of the NMR signal data from the spin echoes RN1, RN2, RN3, . . . ). Similarly, resistivity signals RS21, RS22, RS23, . . . are acquired during the transmission of NMR refocusing pulses T1, T2, T3, . . . ; resistivity signals RS31, RS32, RS33, . . . are acquired during the transmission of NMR refocusing pulses T1, T2, T3, . . . ; and resistivity signals RS41, RS42, RS43, . . . are also acquired during the transmission of NMR refocusing pulses T1, T2, T3, . . . . These resistivity signals RS11-RS13, RS21-RS23, RS31-RS33, and RS41-RS43 . . . are transferred to the resistivity signal processor 552 via the multiplexers 547, 548, 549, and 550; and the receivers 543, 544, 545, and 546, respectively.

In addition to acquiring cross-antenna signals (as described above) single sensor resistivity measurements are also possible, perhaps used to target resistivity measurements that are made in close proximity to the antenna (e.g., at the borehole wall and in nearby formation regions). The resistivity measurement can be accomplished by relating it to the measured effect on the quality factor Q of the measuring antenna, as it is affected by RF losses due to conductivity of the nearby surroundings.

In some embodiments, a single transceiver antenna can be used to determine the resistivity of the environment proximate to the transceiver antenna making the measurement. For example, the resistivity may be assessed by measuring the antenna quality factor Q, perhaps by injecting a CW RF current signal into the antenna and measuring the antenna voltage in response to the injected signal. Alternatively, the signal may be injected in the form of pulses and the transient decay signal provided as a response from the antenna is measured. In some embodiments, CW and/or pulsed RF signals can be injected during the time interval between the RF pulse sequences used for making NMR measurements.

As an indicator of the local formation properties (e.g. fluid type) the resistivity measurements obtained from proximate elements, such as drilling mud or formations near the well bore, can be useful in interpreting NMR measurements. For example, a CW signal generated between NMR pulse sequences could form part of a common signal. This signal could be used for resistivity measurement. In this embodiment, a multiplexer circuit (not shown in FIG. 5) could be inserted to allow the transceiver 118 in FIG. 5 to be switched between NMR sequences in a transmit mode, an NMR receive mode, and a CW signal transmit mode for making resistivity measurements. Still further embodiments may be realized.

Figure 7:
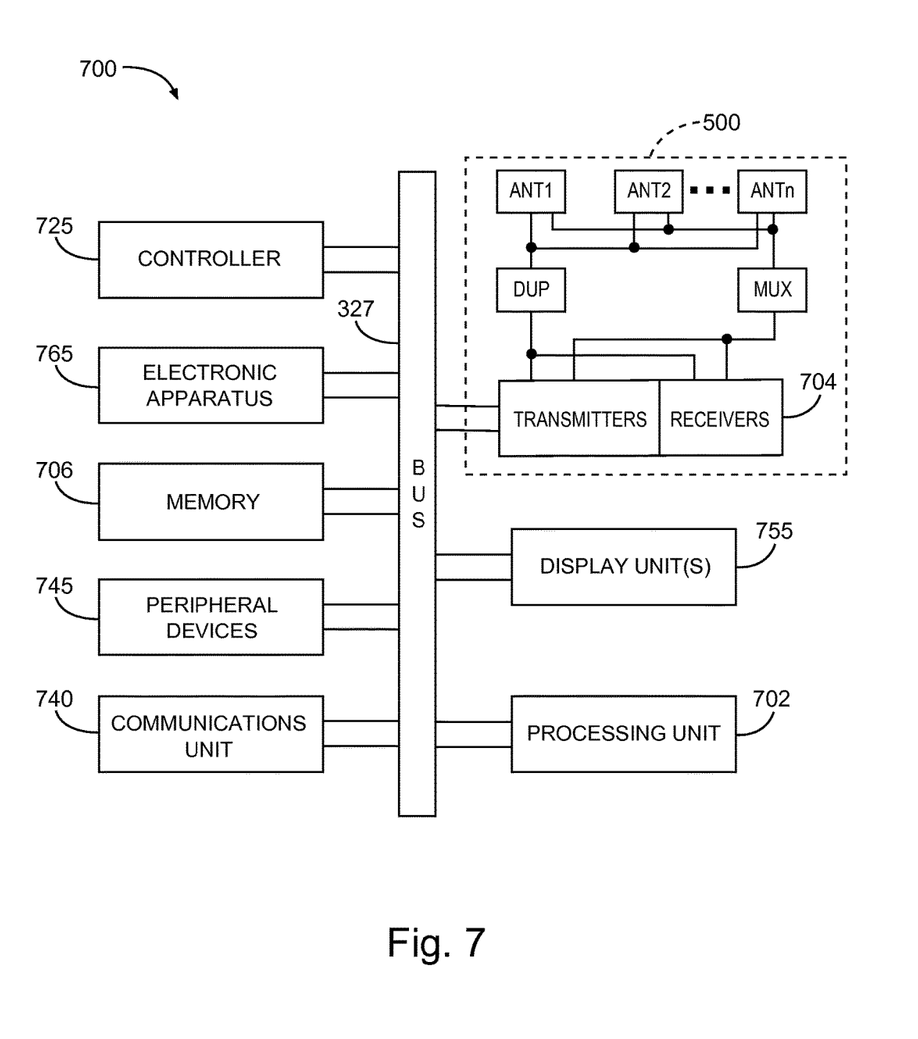
FIG. 7 is a block diagram of a logging system according to various embodiments of the invention.

For example, FIG. 7 is a block diagram of a logging system 700 according to various embodiments of the invention. Referring now to FIGS. 4, 5, and 7 it can be seen that the logging system 700 is closely aligned with the structure and function of the apparatus 100 in FIGS. 4 and 5, as well as the system 500 in FIG. 5. Here the transceiver antennae ANT1, ANT2, . . . ANTn in FIG. 7 comprise multiple transceiver antennae, similar to or identical to the transceiver antennae 113, 114, 118, 119, 220, 221 in FIG. 5. The duplexer unit DUP in FIG. 7 comprises one or more duplexers similar to or identical to the duplexer 541 in FIG. 5. The multiplexer unit MUX in FIG. 7 comprises one or more multiplexers similar to or identical to the multiplexers 547, 548, 549, and 550 in FIG. 5. The transmitter and receiver unit 704 in FIG. 7 comprises one or more transmitters and one or more receivers, similar to or identical to the transmitter 540 and receivers 542, 543, 544, 545, and 546 in FIG. 5. The processing unit 702 in FIG. 7 comprises one or more of the NMR signal processors 551 and resistivity signal processor 552 in FIG. 5.

Referring now to FIGS. 1, 4-5, and 7, it can be seen that the processing unit 702 can couple to the system 500 to obtain NMR and resistivity measurements from the system 500 and apparatus 100 included therein. In some embodiments, a logging system 700 comprises one or more of the systems 500, including a common substrate 104 comprising one or more pieces of pipe, magnets 122, 124, 126, and 128, etc. that can be attached to and thereby convey/protect/contain the antennae 113, 114, 118, 119, 220, 221 and other elements present in the system 500. The housing might take the form of a wireline tool body, or a downhole tool as described in more detail below with reference to FIGS. 9 and 10. The processing unit 702 may be part of a surface workstation or attached to a downhole tool housing. In some embodiments, the processing unit 702 is packaged within the apparatus 100, or the system 500.

The logging system 700 can include a controller 725, other electronic apparatus 765, and a communications unit 740. The controller 725 and the processing unit 702 can be fabricated to operate one or more components of the apparatus 100 and system 500 to acquire measurement data, such as NMR measurements and resistivity measurements.

Electronic apparatus 765 (e.g., electromagnetic sensors, etc.) can be used in conjunction with the controller 725 to perform tasks associated with taking NMR and resistivity measurements downhole. The communications unit 740 can include downhole communications in a drilling operation. Such downhole communications can include a telemetry system.

The logging system 700 can also include a bus 727 to provide common electrical signal paths between the components of the logging system 700. The bus 727 can include an address bus, a data bus, and a control bus, each independently configured. The bus 727 can also use common conductive lines for providing one or more of address, data, or control, the use of which can be regulated by the controller 725.

The bus 727 can include instrumentality for a communication network. The bus 727 can be configured such that the components of the logging system 700 are distributed. Such distribution can be arranged between downhole components such as the apparatus 100 and system 500, and components that can be disposed on the surface of a well. Alternatively, several of these components can be co-located, such as on one or more collars of a drill string or on a wireline structure.

In various embodiments, the logging system 700 includes peripheral devices that can include displays 755, additional storage memory, or other control devices that may operate in conjunction with the controller 725 or the processing unit 702. The display 755 can display diagnostic information for the system 500 based on the signals generated according to embodiments described above. The display 755 can also be used to display one or more sensitivity plots 300, similar to or identical to what is illustrated in FIG. 3.

In an embodiment, the controller 725 can be fabricated to include one or more processors. The display 755 can be fabricated or programmed to operate with instructions stored in the processing unit 702 (for example in the memory 706) to implement a user interface to manage the operation of the system 500 or components distributed within the logging system 700. This type of user interface can be operated in conjunction with the communications unit 740 and the bus 727. Various components of the logging system 700 can be integrated with the system 500 or the associated housing such that processing identical to or similar to the methods discussed with respect to various embodiments herein can be performed downhole.

In various embodiments, a non-transitory machine-readable storage device can include instructions stored thereon, which, when performed by a machine, cause the machine to become a customized, particular machine that performs operations comprising one or more activities similar to or identical to those described with respect to the methods and techniques described herein. A machine-readable storage device, herein, is a physical device that stores information (e.g., instructions, data), which when stored, alters the physical structure of the device. Examples of machine-readable storage devices include, but are not limited to, memory 706 in the form of read only memory (ROM), random access memory (RAM), a magnetic disk storage device, an optical storage device, a flash memory, and other electronic, magnetic, or optical memory devices, including combinations thereof.

The physical structure of stored instructions may thus be operated on by one or more processors such as, for example, the processing unit 702. Operating on these physical structures can cause the machine to perform operations according to methods described herein. The instructions can include instructions to cause the processing unit 702 to store associated data or other data in the memory 706. The memory 706 can store the results of measurements of formation parameters or parameters of the system 500, to include gain parameters, calibration constants, identification data, etc. The memory 706 can store a log of the NMR measurements and resistivity measurements obtained by the system 500. The memory 706 therefore may include a database, for example a relational database.

Figure 8:
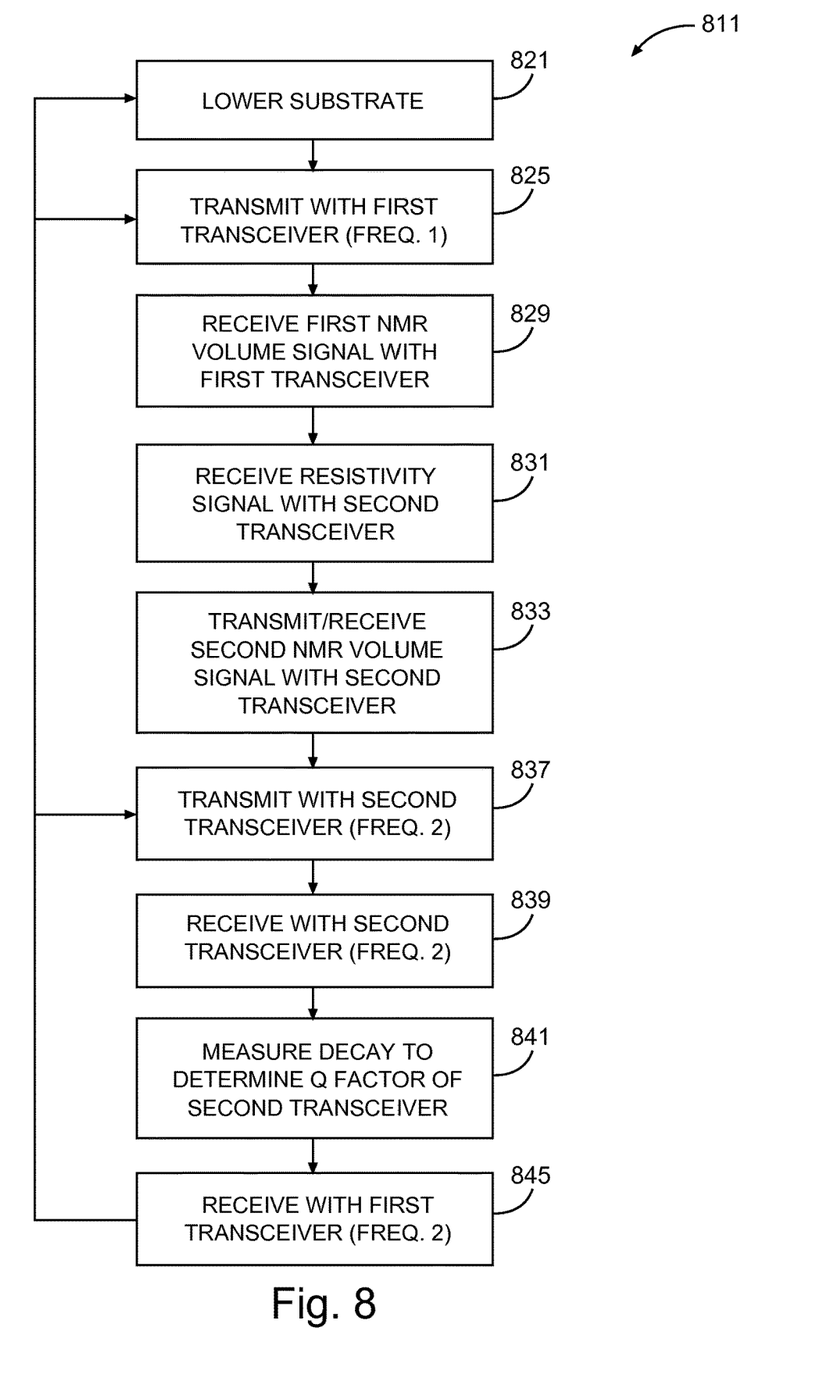
FIG. 8 is a flow diagram illustrating methods of transceiver antenna operation, with multi-volume sensitivity, according to various embodiments of the invention.

FIG. 8 is a flow diagram illustrating methods 811 of transceiver antenna operation, with multi-volume sensitivity, according to various embodiments of the invention. The methods 811 described herein are with reference to hardware circuitry, measurements, switching, transmission, and reception, etc. shown in FIGS. 1-6. Some operations of the methods 811 can be performed in whole or in part by the processing unit 702 or controller 725 (FIG. 7), although many embodiments are not limited thereto.

In some embodiments, a method 811 comprises transmitting a common signal at block 825, and receiving a first NMR volume signal with first transceiver, as well as a resistivity signal at block 831. Many variations may be realized.

For example, the method 811 may be carried out as part of a drilling operation, or a wireline logging operation. Thus, in some embodiments a method 811 may begin at block 821 with lowering a common substrate 104 (reference FIG. 1), into a borehole, the common substrate being attached to first and second transceiver antennae. The common substrate might comprise one of a drill string or a wireline sonde.

The method 811 may continue on to block 825 with transmitting, using the first transceiver antenna, a common signal into a geological formation.

The method 811 may further include, in response to the transmitting at block 825, receiving a first corresponding NMR signal from a first volume of the formation at the first transceiver antenna, at block 829.

A duplexer may be used for both transmitting and receiving activities in some embodiments. Thus, the activity at block 829 may comprise receiving the first corresponding NMR signal through a duplexer that is also used to receive the common signal from the first transceiver antenna.

The method 811 may continue on to block 831 to include, in response to the transmitting at block 825, receiving the common signal transformed by the formation into a received resistivity signal at a second transceiver antenna spaced apart from the first transceiver antenna.

The method 811 may continue on to block 833 to include transmitting and receiving, using the second transceiver antenna, a second NMR signal into a second volume of the formation (i.e., different from the first volume of the formation).

The activities at blocks 825, 829, 831, and 833 may occur using the same frequency FREQ1, or different frequencies.

Multiple measurements of a single antenna resistivity signal can be made to determine the decay rate of the signal, which in turn can be used to determine a quality factor Q of the single antenna, to determine resistivity of the borehole mud or/and nearby formations. Thus, the method 811 may continue on to block 837, to include transmitting a decay signal that will eventually be measured by the same transceiver antenna that transmitted the signal. The activity at block 837 may also be used to include transmitting another signal into the geological formation, perhaps using the second transceiver antenna, for other purposes, such as cross-transceiver signaling.

Each of the transceiver antennae can be used at different frequencies. Thus, the activity conducted as part of the activities shown in blocks 821-833 may include transmitting a common signal at a first frequency (FREQ1), and the activity conducted as part of the activities shown in blocks 837, 839, 841, and 845 may include transmitting a common signal at a second frequency (FREQ2, different from the first frequency FREQ1).

The method 811 may continue on from block 837 to block 839 to include receiving the signal in response to transmitting in block 837, using the same transceiver antenna that was used to transmit the signal.

The method 811 may continue on to block 841 to include measuring the decay rate of a decay signal separately transmitted and received using the second transceiver antenna to determine a quality factor Q of the second transceiver antenna.

It should be noted that the signal transmitted at block 837, and received at block 839 is termed a "decay signal" as a matter of convenience, since it's decay can be measured to determine the quality factor Q of the associated transceiver antenna. However, this signal has other uses, and thus, is not to be so limited.

For example, cross-transceiver signaling can be implemented. Signals may be launched from any one transceiver, and received by another transceiver. Thus, in an embodiment, the second transceiver antenna may be used as a transmitter, and the first transceiver antenna may be used as a receiver (e.g., to receive the signal provided by the second transceiver antenna in block 837). Any one or more of the activities shown in the method 811 may be repeated as desired.

Thus, it should be noted that the methods described herein do not have to be executed in the order described, or in any particular order, unless explicitly specified as such. Moreover, various activities described with respect to the methods identified herein can be executed in iterative, serial, or parallel fashion. Information, including parameters, commands, operands, and other data, can be sent and received in the form of one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that may be employed to create one or more software programs designed to implement and perform the methods disclosed herein. For example, the programs may be structured in an object-orientated format using an object-oriented language such as Java or C#. In another example, the programs can be structured in a procedure-orientated format using a procedural language, such as assembly or C. The software components may communicate using any of a number of mechanisms well known to those of ordinary skill in the art, such as application program interfaces or interprocess communication techniques, including remote procedure calls. The teachings of various embodiments are not limited to any particular programming language or environment. Thus, other embodiments may be realized.

Figure 9:
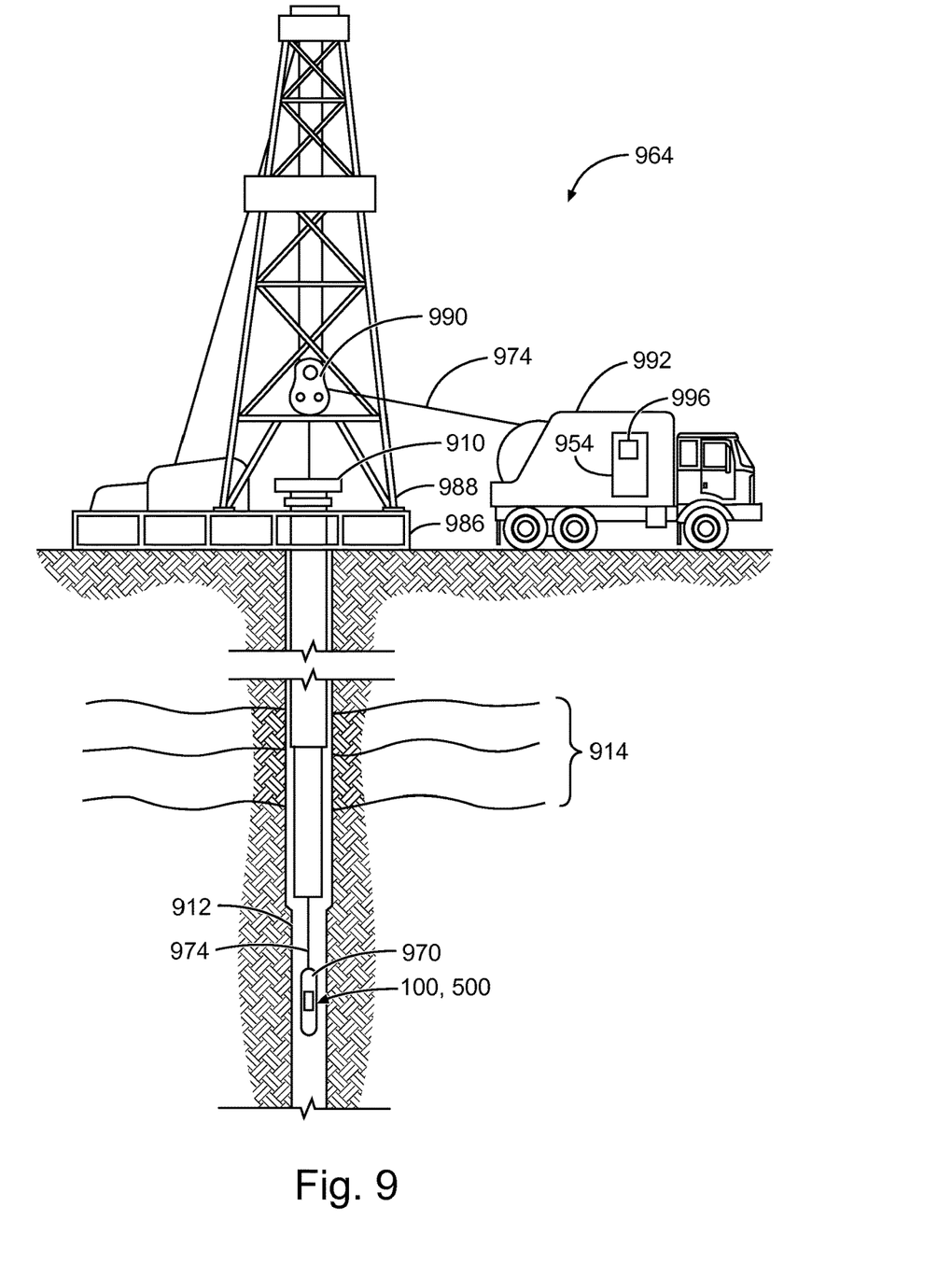
FIG. 9 depicts an example wireline system, according to various embodiments of the invention.
Figure 10:
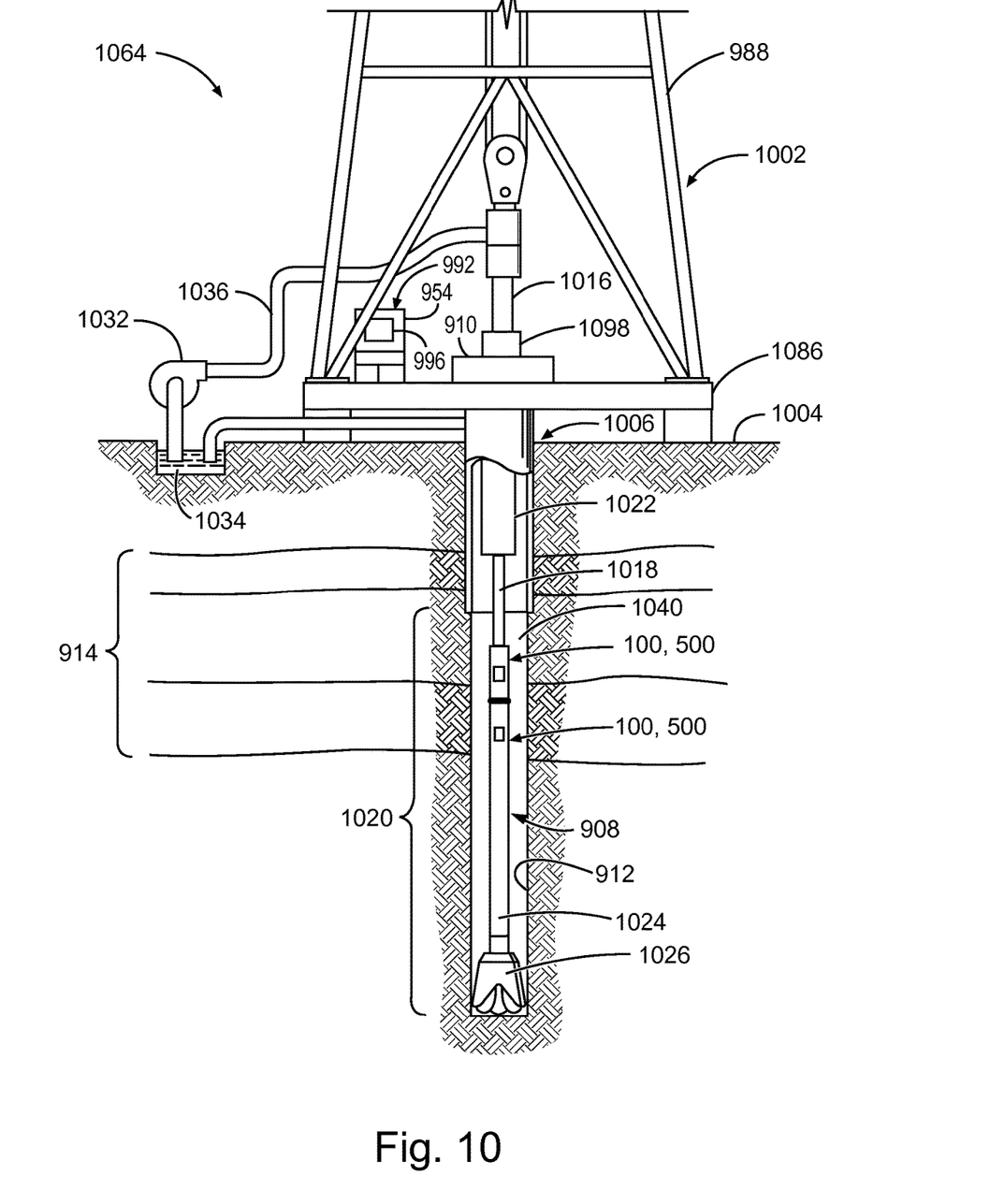
FIG. 10 depicts an example drilling rig system, according to various embodiments of the invention.

For example, FIG. 9 depicts an example wireline system 964, according to various embodiments of the invention. FIG. 10 depicts an example drilling rig system 1064, according to various embodiments of the invention. Either of the systems in FIG. 9 and FIG. 10 are operable to control a combined NMR-resistivity apparatus 100 and/or measurement system 500 to conduct measurements in a wellbore. Thus, the systems 964, 1064 may comprise portions of a wireline logging tool body 970 as part of a wireline logging operation, or of a downhole tool 1024 (e.g., a drilling operations tool) as part of a downhole drilling operation.

Returning now to FIG. 9, a well during wireline logging operations can be seen. In this case, a drilling platform 986 is equipped with a derrick 988 that supports a hoist 990.

Drilling oil and gas wells is commonly carried out using a string of drill pipes connected together so as to form a drilling string that is lowered through a rotary table 910 into a wellbore or borehole 912. Here it is assumed that the drilling string has been temporarily removed from the borehole 912 to allow a wireline logging tool body 970, such as a probe or sonde, to be lowered by wireline or logging cable 974 into the borehole 912. Typically, the wireline logging tool body 970 is lowered to the bottom of the region of interest and subsequently pulled upward at a substantially constant speed.

During the upward trip, at a series of depths the instruments (e.g., the apparatus 100 or system 500 shown in FIGS. 4 and 5) included in the tool body 970 may be used to perform measurements on the subsurface geological formations adjacent the borehole 912 (and the tool body 970, which can serve as a common substrate for the various transceiver antennae of the apparatus). The measurement data can be communicated to a surface logging facility 992 for storage, processing, and analysis. The logging facility 992 may be provided with electronic equipment for various types of signal processing, which may be implemented by any one or more of the components of the combined NMR-resistivity measurement apparatus 100 and system 500. Similar formation evaluation data may be gathered and analyzed during drilling operations (e.g., during LWD operations, and by extension, sampling while drilling).

In some embodiments, the tool body 970 comprises a combined NMR-resistivity measurement apparatus 100 and/or system 500 for obtaining and analyzing NMR and resistivity measurements in a subterranean formation through a borehole 512. The tool is suspended in the wellbore by a wireline cable 974 that connects the tool to a surface control unit (e.g., comprising a workstation 954, which can also include a display). The tool may be deployed in the borehole 912 on coiled tubing, jointed drill pipe, hard wired drill pipe, or any other suitable deployment technique.

Turning now to FIG. 10, it can be seen how a system 1064 may also form a portion of a drilling rig 1002 located at the surface 1004 of a well 1006. The drilling rig 1002 may provide support for a drill string 1008. The drill string 1008 may operate to penetrate the rotary table 910 for drilling the borehole 912 through the subsurface formations 914. The drill string 1008 may include a Kelly 1016, drill pipe 1018, and a bottom hole assembly 1020, perhaps located at the lower portion of the drill pipe 1018.

The bottom hole assembly 1020 may include drill collars 1022, a downhole tool 1024, and a drill bit 1026. The drill bit 1026 may operate to create the borehole 912 by penetrating the surface 1004 and the subsurface formations 1014. The downhole tool 1024 may comprise any of a number of different types of tools including MWD tools, LWD tools, and others.

During drilling operations, the drill string 1008 (perhaps including the Kelly 1016, the drill pipe 1018, and the bottom hole assembly 1020) may be rotated by the rotary table 910. Although not shown, in addition to, or alternatively, the bottom hole assembly 1020 may also be rotated by a motor (e.g., a mud motor) that is located downhole. The drill collars 1022 may be used to add weight to the drill bit 1026. The drill collars 1022 may also operate to stiffen the bottom hole assembly 1020, allowing the bottom hole assembly 1020 to transfer the added weight to the drill bit 1026, and in turn, to assist the drill bit 1026 in penetrating the surface 1004 and subsurface formations 1014.

During drilling operations, a mud pump 1032 may pump drilling fluid (sometimes known by those of ordinary skill in the art as "drilling mud") from a mud pit 1034 through a hose 1036 into the drill pipe 1018 and down to the drill bit 1026. The drilling fluid can flow out from the drill bit 1026 and be returned to the surface 1004 through an annular area 1040 between the drill pipe 1018 and the sides of the borehole 912. The drilling fluid may then be returned to the mud pit 1034, where such fluid is filtered. In some embodiments, the drilling fluid can be used to cool the drill bit 1026, as well as to provide lubrication for the drill bit 1026 during drilling operations. Additionally, the drilling fluid may be used to remove subsurface formation cuttings created by operating the drill bit 1026.

Thus, it may be seen that in some embodiments, the systems 964, 1064 may include a drill collar 1022, a downhole tool 1024, and/or a wireline logging tool body 970 to house one or more combined NMR-resistivity measurement apparatus 100, similar to or identical to the apparatus 100 described above and illustrated in FIG. 4. Components of the system 500 in FIG. 5 may also be attached to or housed by the tool 1024 or the tool body 970, to be constructed and operated as described previously.

Thus, for the purposes of this document, the term "common substrate" may include any one or more of a drill collar 1022, a downhole tool 1024, or a wireline logging tool body 970, all having an outer wall that is shared among a number of components. Thus, a common substrate is used to enclose or attach to magnetometers, sensors, fluid sampling devices, pressure measurement devices, transceiver antennae, transmitters, receivers, acquisition and processing logic, and data acquisition systems. The tool 1024 may comprise a downhole tool, such as an LWD tool or MWD tool. The wireline tool body 970 may comprise a wireline logging tool, including a probe or sonde, for example, coupled to a logging cable 974. Many embodiments may thus be realized.

In some embodiments, the apparatus 100 may be constructed in the form of a downhole tool. Thus, referring to FIGS. 1-5 it can be seen that an apparatus 100 may comprise a pair of transceiver antennae; each provides a separate NMR sensitivity volume, and each can be operated to obtain resistivity measurements. That is, an apparatus 100 may comprise a first transceiver antenna 113 to transmit a common signal into a geological formation, and to receive a first corresponding nuclear magnetic resonance (NMR) signal from a first volume of the formation. The apparatus 100 may comprise a second transceiver antenna 118 to receive a resistivity signal as a version of the common signal transformed by the formation, and to transmit and receive a second NMR signal from a second volume of the formation different from the first volume of the formation.

In most embodiments, a common substrate is used to mount both antennae. Thus, the apparatus 100 may comprise a common substrate 104 having a longitudinal axis, wherein the first and second transceiver antennae 113, 118 are attached to the common substrate.

The antennae may have axes of primary sensitivity that are substantially perpendicular to each other. Thus, the first transceiver antenna 113 has a primary axis of sensitivity 446 substantially transverse to the longitudinal axis 450, and wherein the second transceiver antenna 118 has a primary axis of sensitivity 444 substantially parallel to the longitudinal axis 450.

The common substrate may be tubular in form, and a transceiver antenna may take the form of a saddle coil. Thus, in some embodiments, the common substrate 104 comprises a substantially tubular substrate, and the first transceiver antenna 113 comprises one of a pair of overlapping transverse saddle coils (e.g., antennae 113, 114) mounted on or within a wall of the common substrate 104. In some embodiments, one or the other, or both of the saddle coils (e.g., antennae 113, 114) are formed as a single- or multi-turn coil inside of the cylindrical surface structure.

A transceiver coil may be disposed between a pair of coils that form a monopole antenna when connected in reverse polarity (see especially FIG. 2). Thus, in some embodiments, the second transceiver antenna may comprise one of a pair of coils 220, 221 separated from each other to define a space in which the first transceiver antenna is disposed, and wherein the pair of coils, when connected in reverse polarity, form a monopole antenna.

The directions of magnetic fields in different volumes can be specified. For example, longitudinal fields can be generated, in contrast to prior art configurations. Thus, in some embodiments, azimuthal selectivity for both the NMR signal and the resistivity signal are provided by exciting the first and second transceiver antennae comprising a combination of transverse saddle coils 113, 114 and a monopole antenna comprising a combination of the two coils forming longitudinal dipole antennae 220, 221.

In some embodiments, the first transceiver antenna is part of a saddle coil pair, and the second transceiver antenna is part of a loop coil pair. Thus, the first transceiver antenna may be formed, in part, by a quadrature coil pair of overlapping saddle coils 113, 114.

The apparatus 100 may comprise a second pair of non-overlapping loop coils 220, 221 disposed along a common axis (e.g., the longitudinal axis 450) in parallel with the first pair of non-overlapping loop coils 118, 119. The coils 220, 221 forming different antennae can be combined to make a monopole antenna. Still more embodiments may be realized.

For example, referring to FIGS. 5, 7, and 9-10, it can be seen that a system 500, 964, 1064 may comprise a downhole tool housing having a longitudinal axis; and one or more transceiver antennae (e.g., antennae 113, 114, 118, 119, 220, 221) attached to the housing, to operate as described previously. The downhole tool housing may comprise one of a wireline tool housing or a drill string tool housing.

A multiplexer may be connected to the transceiver and combination antennae. Thus, in some embodiments, the system 500, 964, 1064 includes at least one multiplexer 547-550 coupled to the first and second transceiver antennae 113, 118.

A controller may be used to determine whether the antennae are operating in a transmission or reception mode. Thus, in some embodiments, a controller 725 is operably connected to the first transceiver antenna 113 to enable the first transceiver antenna to transmit a common signal and to receive a corresponding NMR signal. Individual transceiver antennae may be formed as single- or multi-turn solenoid-type coils.

Any of the above components, for example the combined NMR-resistivity ray measurement apparatus 100 (and each of its elements), the systems 500, 964, 10664 (and each of their elements) may all be characterized as "modules" herein. Such modules may include hardware circuitry, and/or a processor and/or memory circuits, software program modules and objects, and/or firmware, and combinations thereof, as desired by the architect of the apparatus 100 and systems 500, 964, 1064 and as appropriate for particular implementations of various embodiments. For example, in some embodiments, such modules may be included in an apparatus and/or system operation simulation package, such as a software electrical signal simulation package, an NMR-resistivity signal propagation package, a power usage and distribution simulation package, a power/heat dissipation simulation package, a measured radiation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of the apparatus 100 and systems 500, 964, 1064 are intended to provide a general understanding of the structure of various embodiments, and they are not intended to serve as a complete description of all the elements and features of apparatus and systems that might make use of the structures described herein.

In summary, using the apparatus, systems, and methods disclosed herein may provide a compact antennae configuration that is capable of providing a combined NMR-resistivity measurements over multiple NMR sensitivity volumes. This is a practical solution that combines azimuthally-resolved NMR and resistivity measurements in a single tool without increasing the length, complexity, and cost of LWD equipment. These advantages can significantly enhance the value of the services provided by an operation/exploration company, helping to reduce costs and increase customer satisfaction. A list of additional possible embodiments is now presented.

In some embodiments, an apparatus comprises a first transceiver antenna to transmit a common signal into a geological formation, and to receive a first corresponding nuclear magnetic resonance (NMR) signal from a first volume of the formation. The apparatus also comprises a second transceiver antenna to receive a resistivity signal as a version of the common signal transformed by the formation, and to transmit and receive a second NMR signal from a second volume of the formation different from the first volume of the formation.

In some embodiments, the apparatus comprises a common substrate having a longitudinal axis, wherein the first and second transceiver antennae are attached to the common substrate. The common substrate may comprise any number and type of housing, including pipe sections joined together in a drill string. Thus, the common substrate comprises a substantially tubular substrate in some embodiments.

The antennae may be formed as solenoid-type coils, or saddle coils, including multi-turn saddle coils. A quadrature coil pair of overlapping saddle coils may be used to form part of the first transceiver antenna, and non-overlapping solenoid-type coils may be used to from part of the second transceiver antenna.

In some embodiments, coils are combined to form a single transceiver antenna. For example, in some embodiments, the second transceiver antenna comprises one of a pair of coils separated from each other to define a space in which the first transceiver antenna is disposed, and the pair of coils that form the second transceiver antenna, when connected in reverse polarity, form a monopole antenna. In some embodiments, azimuthal selectivity for both the NMR signal and the resistivity signal are provided by transmitting and/or receiving with the first and second transceiver antennae comprising a combination of transverse saddle coils and a monopole antenna.

In some embodiments, the first transceiver antenna has a primary axis of sensitivity substantially transverse to the longitudinal axis, and the second transceiver antenna has a primary axis of sensitivity substantially parallel to the longitudinal axis.

The first transceiver antenna may comprise one of a pair of overlapping transverse saddle coils mounted on or within a wall of the common substrate, in some embodiments. Thus, driving the coils with 90° phase-shifted RF pulses can provide a circular polarized NMR excitation. The overlapping transverse saddle coils can be also used for quadrature coil detection of NMR signals. Both circular polarization and quadrature coil detection can operate to make the NMR sensor more efficient.

In some embodiments, a system comprise a downhole tool housing having a longitudinal axis, and one or more transceiver antennae. The downhole tool housing may comprise one of a wireline tool housing or a drill string tool housing, including drill collars, subs, and other components of a bottom hole assembly.

For example, a first transceiver antenna may be attached to the housing, the first transceiver antenna capable of transmitting a common signal into a geological formation, and to receive a first corresponding nuclear magnetic resonance (NMR) signal from a first volume of the formation. A second transceiver antenna may also be attached to the housing, the second transceiver antenna being capable of receiving a resistivity signal as a version of the common signal transformed by the formation, and generating and receiving a second corresponding NMR signal from a second volume of the formation different from the first volume of the formation.

The system may comprise one or more multiplexers, coupled to the first and/or second transceiver antennae, as well as other antennae.

The system may comprise one or more controllers, operably connected to the first transceiver antenna to enable the first transceiver antenna to transmit the common signal and to receive the first corresponding NMR signal. The controllers may also be operably connected to other transceiver antenna to transmit and receive signals that enable NMR and resistivity measurements over multiple sensitivity volumes.

Methods may comprise a wide variety of activities, including transmitting, using a first transceiver antenna, a common signal into a geological formation; and receiving in response to the transmitting, at the first transceiver antenna, a first corresponding nuclear magnetic resonance (NMR) signal from a first volume of the formation. Methods may further include receiving, in response to the transmitting, at a second transceiver antenna spaced apart from the first transceiver antenna, the common signal transformed by the formation into a received resistivity signal; and receiving at the second transceiver antenna, a second NMR signal from a second volume of the formation different from the first volume of the formation. Depending on the construction of the apparatus and system, receiving the first corresponding NMR signal may further comprise receiving the first corresponding NMR signal through a duplexer that is also used to receive the common signal from the first transceiver antenna.

Some methods include lowering a common substrate (e.g., a housing) into a borehole, the common substrate attached to the first and second transceiver antennae, wherein the common substrate comprises one of a drill string or a wireline sonde.

Some methods include measuring the decay rate of a decay signal separately transmitted and received using the second transceiver antenna to determine a quality factor of the second transceiver antenna. The quality factor Q can in turn be used to determine resistivity of the environment proximate to the transceiver antenna making the measurement.

Different frequencies can be used for excitation and reception. Thus, in some embodiments, the common signal is transmitted at a first frequency, and wherein the other signal is transmitted at a second frequency different from the first frequency. Many more embodiments may be realized, but have not been explicitly listed here in the interest of brevity.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:
    a first transceiver antenna configured to transmit a first common signal into a geological formation, and to receive a first corresponding nuclear magnetic resonance (NMR) signal from a first volume of the formation; and
    a second transceiver antenna comprising one of a pair of coils separated from each other to define a space in which the first transceiver antenna is disposed, and wherein the pair of coils, when connected in reverse polarity, form a monopole antenna, said second transceiver antenna configured to,
        receive a resistivity signal from the formation corresponding to the first common signal;
        transmit a second common signal into the geological formation; and
        receive a second corresponding NMR signal from a second volume of the formation.

2. The apparatus of claim 1, further comprising:
    a common substrate having a longitudinal axis, wherein the first and second transceiver antennae are attached to the common substrate, and wherein the first transceiver antenna has a first primary axis of sensitivity substantially transverse to the longitudinal axis, and wherein the second transceiver antenna has a second primary axis of sensitivity substantially parallel to the longitudinal axis.

3. The apparatus of claim 1, wherein the common substrate comprises a substantially tubular substrate, and wherein the first transceiver antenna comprises one of a pair of overlapping transverse saddle coils mounted on or within a wall of the common substrate.

4. The apparatus of claim 1, wherein the first transceiver antenna is formed as a multi-turn saddle coil.

5. The apparatus of claim 1, wherein azimuthal selectivity for both the NMR signal and the resistivity signal are provided by exciting the first and second transceiver antennae comprising a combination of transverse saddle coils and a monopole antenna comprising two longitudinal dipole antennae.

6. The apparatus of claim 1, further comprising:
a quadrature coil pair of overlapping saddle coils forming part of the first transceiver antenna; and
a first pair of non-overlapping loop coils forming part of the second transceiver antenna.

7. The apparatus of claim 6, further comprising
a second pair of non-overlapping loop coils disposed along a common axis in parallel with the first pair of non-overlapping loop coils.

8. The apparatus of claim 1, wherein the second common signal is orthogonal to the first common signal.

9. A system, comprising:
a downhole tool housing having a longitudinal axis;
a first transceiver antenna attached to the housing, the first transceiver antenna configured to transmit a first common signal into a geological formation, and to receive a first corresponding nuclear magnetic resonance (NMR) signal from a first volume of the formation; and
a second transceiver antenna attached to the housing, the second transceiver antenna configured to receive a resistivity signal from the formation corresponding to the first common signal, and to transmit a second common signal and receive a second corresponding NMR signal from a second volume of the formation, wherein the second transceiver antenna comprises one of a pair of coils separated from each other to define a space in which the first transceiver antenna is disposed, and wherein the pair of coils, when connected in reverse polarity, form a monopole antenna.

10. The system of claim 9, further comprising:
at least one multiplexer coupled to the first and second transceiver antennae.

11. The system of claim 9, further comprising:
a controller operably connected to the first transceiver antenna to enable the first transceiver antenna to transmit the common signal and to receive the first corresponding NMR signal.

12. The system of claim 9, wherein the downhole tool housing comprises one of a wireline tool housing or a drill string tool housing.

13. The system of claim 9, wherein at least a portion of the second transceiver antenna comprises a helical coil.

14. An apparatus, comprising:
a first transceiver antenna configured to transmit a first common signal into a geological formation, and to receive a first corresponding nuclear magnetic resonance (NMR) signal from a first volume of the formation; and
a second transceiver antenna configured to,
receive a resistivity signal from the formation corresponding to the first common signal;
transmit a second common signal into the geological formation; and
receive a second corresponding NMR signal from a second volume of the formation, wherein azimuthal selectivity for both the NMR signal and the resistivity signal are provided by using the first and second transceiver antennae comprising a combination of transverse saddle coils and a monopole antenna comprising two longitudinal dipole antennae.

15. The apparatus of claim 14, further comprising:
a common substrate having a longitudinal axis, wherein the first and second transceiver antennae are attached to the common substrate, and wherein the first transceiver antenna has a first primary axis of sensitivity substantially transverse to the longitudinal axis, and wherein the second transceiver antenna has a second primary axis of sensitivity substantially parallel to the longitudinal axis.

16. The apparatus of claim 14, wherein the common substrate comprises a substantially tubular substrate, and wherein the first transceiver antenna comprises one of a pair of overlapping transverse saddle coils mounted on or within a wall of the common substrate.

17. The apparatus of claim 14, wherein the first transceiver antenna is formed as a multi-turn saddle coil.

18. The apparatus of claim 14, wherein the second transceiver antenna comprises one of a pair of coils separated from each other to define a space in which the first transceiver antenna is disposed, and wherein the pair of coils, when connected in reverse polarity, form a monopole antenna.

19. The apparatus of claim 14, further comprising:
a quadrature coil pair of overlapping saddle coils forming part of the first transceiver antenna; and
a first pair of non-overlapping loop coils forming part of the second transceiver antenna.

* * * * *